United States Patent
Leavitt et al.

(10) Patent No.: US 10,172,629 B2
(45) Date of Patent: *Jan. 8, 2019

(54) SYSTEMS AND METHODS FOR IMPLANTING SURGICAL IMPLANTS

(71) Applicant: Orthopro LLC, Salt Lake City, UT (US)

(72) Inventors: Dustin D. Leavitt, Oakley, UT (US); Brock L. Johnson, Draper, UT (US); Wesley N. Harris, Marion, UT (US)

(73) Assignee: Orthopro LLC, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/710,339

(22) Filed: Sep. 20, 2017

(65) Prior Publication Data
US 2018/0028201 A1 Feb. 1, 2018

Related U.S. Application Data

(63) Continuation of application No. 13/541,505, filed on Jul. 3, 2012, now Pat. No. 9,775,630.

(60) Provisional application No. 61/651,219, filed on May 24, 2012.

(51) Int. Cl.
| | | |
|---|---|---|
| *A61B 17/16* | (2006.01) | |
| *A61B 17/88* | (2006.01) | |
| *A61B 17/84* | (2006.01) | |
| *A61B 17/72* | (2006.01) | |

(Continued)

(52) U.S. Cl.
CPC ...... *A61B 17/1697* (2013.01); *A61B 17/7291* (2013.01); *A61B 17/848* (2013.01); *A61B 17/8872* (2013.01); *A61B 17/142* (2016.11); *A61B 17/164* (2013.01); *A61B 17/1622* (2013.01); *A61B 17/1682* (2013.01); *A61B 17/1686* (2013.01); *A61B 17/7225* (2013.01); *A61B 2090/036* (2016.02)

(58) Field of Classification Search
CPC . A61B 17/56; A61B 17/7291; A61B 17/8872; A61B 17/1697; A61B 17/848
See application file for complete search history.

(56) References Cited

U.S. PATENT DOCUMENTS

| | | | |
|---|---|---|---|
| 4,128,038 A | * | 12/1978 | Urwin .................. B25B 13/485 411/403 |
| 5,417,692 A | | 5/1995 | Goble et al. |
| 5,919,193 A | | 7/1999 | Slavitt |

(Continued)

OTHER PUBLICATIONS

BioMedical Enterprises, Inc., Hammerlock Nitinol Intramedullary Fixation System, A117-004 (Rev B), copyright 2010 (2 pages).

(Continued)

*Primary Examiner* — Christopher Beccia
(74) *Attorney, Agent, or Firm* — Duane Morris LLP

(57) ABSTRACT

The present invention relates to an implant system that comprises an implant, a handle configured to removably receive the implant, and, in some embodiments, a spacer tool configured to be mounted on the implant. In further embodiments, a k-wire is employed to guide the implant to a desired location. The handle has a hole for receiving a first portion of the implant. Using the handle to implant the implant, along with an associated spacer, provides a quick and convenient method for implanting the implant as described herein and in the associated drawings.

20 Claims, 18 Drawing Sheets

(51) Int. Cl.
*A61B 90/00* (2016.01)
*A61B 17/14* (2006.01)

(56) References Cited

U.S. PATENT DOCUMENTS

| | | | |
|---|---|---|---|
| 6,319,284 | B1 | 11/2001 | Rushdy et al. |
| 6,458,134 | B1 | 10/2002 | Songer et al. |
| 6,500,206 | B1 * | 12/2002 | Bryan ................. A61B 17/025 606/247 |
| 6,517,543 | B1 * | 2/2003 | Berrevoets ............. A61B 17/68 411/324 |
| 8,685,024 | B2 | 4/2014 | Roman |
| 2010/0131014 | A1 | 3/2010 | Peyrot et al. |
| 2011/0276099 | A1 | 11/2011 | Champagne et al. |
| 2011/0301652 | A1 | 12/2011 | Reed et al. |
| 2011/0301653 | A1 | 12/2011 | Reed et al. |
| 2012/0065692 | A1 | 3/2012 | Champagne et al. |
| 2012/0083791 | A1 * | 4/2012 | Cheney ............. A61B 17/8872 606/99 |
| 2012/0089197 | A1 | 4/2012 | Anderson |
| 2012/0150241 | A1 * | 6/2012 | Ragab .................. A61F 2/4611 606/86 A |
| 2013/0066383 | A1 | 3/2013 | Anderson et al. |
| 2013/0123862 | A1 * | 5/2013 | Anderson ............. A61B 17/88 606/321 |

OTHER PUBLICATIONS

OrthoPro LLC, "2.0 and 2.5 mm Cannulated Screws for the Surgical Repaira of Hammer Toes," published, on information and belief, at least as early as 2009 (5 pages).

BioMedical Enterprises. Inc. Hammerlock™ hammerlock® Nitinol Intramedullary Fixation System "Active fixation for every joint of the lesser toes", on information and belief, this reference was available in 2010.

* cited by examiner

SYSTEMS AND METHODS FOR IMPLANTING SURGICAL IMPLANTS

CROSS-REFERENCE TO RELATED APPLICATIONS

This application is a continuation of U.S. application Ser. No. 13/541,505 filed Jul. 3, 2012, which claims priority to U.S. Provisional Patent Application No. 61/651,219, filed on May 24, 2012, the entirety of which are incorporated herein by reference.

BACKGROUND OF THE INVENTION

1. The Field of the Invention

This invention is in the field of surgical implants and methods for implanting the implants.

2. Background and Relevant Art

Surgical implants can be used to fuse or connect portions of bone together. For instance, surgical implant can connect two bone portions, such as portions of joints together. Hence, the surgical implant can remain implanted (e.g., permanently) in a patient's bone portions. In other instances, surgical implants can connect portions of the same bone together (e.g., a broken or shattered bone) to promote healing. Accordingly, some implants can be removable, for example, after the connected portions of the bone have healed.

The fusion or connection of bones often can be a complex process that takes substantial time and a variety of different instruments and devices in order to successfully insert and implant an implant. Furthermore, oftentimes an operating physician may have a single attempt to successfully implant a permanent or semi-permanent implant. For example, after initial insertion or implantation, some implants cannot be easily removed without damaging the patient's bone. Implanting such implants can be an even more demanding and complex procedure and can require substantial manual dexterity and accuracy from the operating physician preforming the procedure.

Accordingly, it is desirable to find an inexpensive and efficient method for implanting implants.

BRIEF SUMMARY OF THE INVENTION

The present invention relates to an implant system that comprises an implant, a handle configured to removably receive the implant, and, in some embodiments, a spacer tool configured to be mounted on the implant. In further embodiments, a k-wire and an associated driving mechanism for driving the k-wire are employed. The handle has a hole therein for receiving a first portion of the implant. Using the handle to implant the implant, along with an associated spacer, provides a quick and convenient method for implanting the implant as described herein and in the associated drawings.

One embodiment includes an implant system for connecting two or more bone portions. The system has an implant having a first portion, a second portion, and an intermediate portion between the first and second portions. Additionally, the system has a handle configured to be grasped by a user for inserting the second portion of the implant into a first bone portion. Furthermore, the handle has a hole therein that is configured to receive the first portion of the implant. Also, the handle is configured to be removed from the first portion of the implant after inserting the second portion of the implant into the first bone portion.

Another embodiment includes a system for correcting a hammer toe condition by fusing a middle phalanx to a proximal phalanx. The system has an implant having a first barbed portion, a second barbed portion and an intermediate portion between the first and second barbed portions. The system also has a handle having a hole configured to receive the first barbed portion, the handle configured to be grasped by a user. Moreover, the system has a spacer configured to be removably coupled to the intermediate portion of the implant. The second barbed portion of the implant is configured to be inserted into one of said middle phalanx or said proximal phalanx. Also, the first barbed portion of the implant is configured to be removed from the handle and then inserted into the other of said middle phalanx or said proximal phalanx.

Still one other embodiment includes a method for implanting an implant between first and second bone portions. The method includes providing an implant having a first portion, a second portion, and an intermediate portion between the first and second portions. The method also includes providing a handle configured to be grasped by a user. The handle has a hole therein that is configured to receive one or more of the first portion, the second portion, and the intermediate portion of the implant. The method further includes positioning at least a part of the first portion of the implant within the hole of the handle, such that a user can grasp the handle and manipulate the implant with the handle. The method also includes inserting the second portion of the implant into the first bone portion, removing the handle from the first portion of the implant, and positioning the first portion of the implant within the second bone portion.

Additional features and advantages of exemplary embodiments of the invention will be set forth in the description which follows, and in part will be obvious from the description, or may be learned by the practice of such exemplary embodiments. The features and advantages of such embodiments may be realized and obtained by means of the instruments and combinations particularly pointed out in the appended claims. These and other features will become more fully apparent from the following description and appended claims, or may be learned by the practice of such exemplary embodiments as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. For better understanding, the like elements have been designated by like reference numbers throughout the various accompanying figures. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1A:
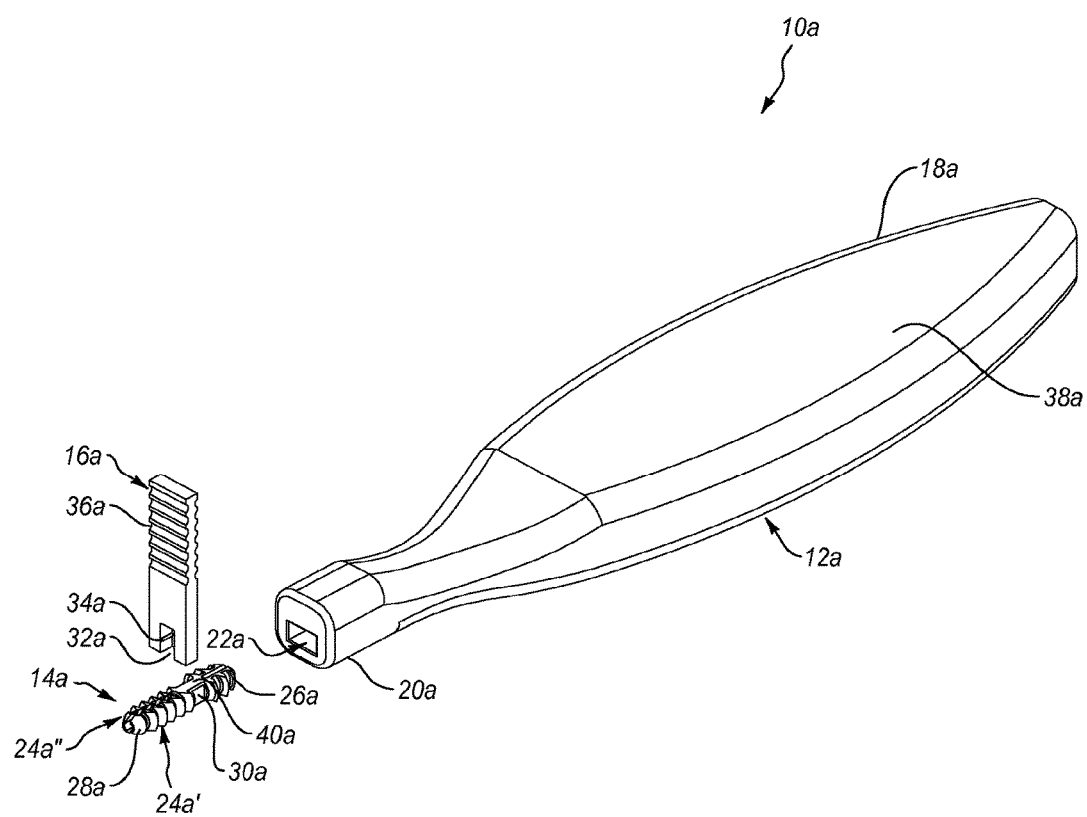
FIG. 1A illustrates a perspective view of an implant system in accordance with one embodiment of the present invention.

The present invention relates to an implant system that comprises an implant, a handle configured to removably receive the implant, and, in some embodiments, a spacer tool configured to be mounted on the implant. In further embodiments, a k-wire and an associated driving mechanism for driving the k-wire are employed. The handle has a hole therein for receiving a first portion of the implant. Using the handle to implant the implant, along with an associated spacer, provides a quick and convenient method for implanting the implant as described herein and in the associated drawings.

The implant system is designed to implant the implant between two bone portions which may be, for example, opposing portions of a joint. The bone portions are prepared for receiving the implant, e.g., by drilling holes to receive the implant. In one embodiment, the first portion of the implant is removably positioned within the handle with the spacer mounted on the implant. A second portion of the implant is then inserted into a first bone portion, such that the spacer abuts an edge of the first bone portion. Thereafter, the handle is removed from the implant. The first portion of the implant, which was previously in the handle, is then positioned within the second bone portion, and, subsequently, the two bone portions are moved together with the spacer remaining therebetween. The spacer provides appropriate spacing between the portions and helps to ensure that the proper portion of the implant is in each bone portion. The spacer is then removed and the bone portions are forced even closer together, with the implant properly placed in respective locations therein to fuse the two bone portions together.

Also, in some embodiments, the implant is barbed on opposing ends, enabling the first portion of the implant to be non-removably inserted within one bone portion, while the second portion is non-removably inserted within another bone portion. The spacer helps to ensure that the second barbed portion of the implant is positioned within the first bone portion, while the first barbed portion of the implant is positioned within the second bone portion, such that the portions of the implant are located in the appropriate bone portions, and such that proper spacing is achieved. In other words, the spacer ensures that a sufficient part of the implant is located within each of the bone portions, such that the implant can securely connect and/or fuse the two bone portions.

Additionally, in one or more embodiments, the implant is a substantially linear implant. Accordingly, the two bone portions connected by linear implant take a substantially linear shape after connection. In other embodiments, however, the implant can be an angled implant, such that the two bone portions connected by the angled implant can form an angled connection.

In another embodiment the implant is a cannulated implant having a passageway therethrough, so as to be properly positioned over a k-wire. Before placing the cannulated implant onto the k-wire, the k-wire is inserted into a bone portion (e.g., at a joint). The first portion of the implant is removably loaded into the handle and, in some instances, a spacer is coupled to the middle portion of the implant (i.e., between barbed portions). Using the handle, the second portion of the implant is fed over the k-wire and into a first bone portion. Then the handle is removed from the implant. The k-wire can be fed into the second, opposing bone portion, and the implant is inserted into the second bone portion. The spacer ensures that the barbed portions of the implant are positioned in the appropriate and respective bone portions. The bone or joint portions are moved together and abut the spacer. Subsequently, the spacer is then removed, and the bone (or joint) portions are moved closer together to facilitate fusion.

In at least one embodiment, the implant system includes a handle preloaded with an implant. The handle and the implant are sterile, such that no further preparation is needed before inserting the second portion of the implant into a first bone portion (i.e., the implant can be immediately inserted into the bone portion). After insertion of the implant, the handle is removed and discarded (e.g., thrown away or sent for recycling or sterilization). Hence, the implant system also can reduce the number of steps required for implanting an implant, for instance, by eliminating the need to position the implant inside the handle.

Referring now to the figures, FIG. 1A illustrates one embodiment of the implant system. In particular, an implant system 10a, illustrated in FIG. 1A, includes a handle 12a, an implant 14a, and a spacer 16a. Notably, however, in other embodiments, the implant system 10a may include only the handle 12a and the implant 14a (i.e., may not include the spacer 16a). The handle 12a has a proximal portion 18a and a distal portion 20a. The handle 12a also has a hole 22a in the distal portion 20a thereof. The hole 22a is configured to accept and facilitate the implant 14a. More specifically, the implant 14a can be removably inserted into the hole 22a. The spacer 16a also can be removably secured or coupled to the implant 14a.

The implant 14a has a substantially linear shape. Accordingly, when used to connect to bone portions, the bone portions connect with the implant 14a form a substantially linear bone connection. The implant 14a also has a plurality of interrupted barbs 24a', 24a" disposed on two opposing sides thereof. In other words, the barbs 24a', 24a" do not encircle the implant 14a (as viewed at an end or cross-sectional view of the implant 14a) and form a section of barbs 24a' and one side of the implant 14a and another section of barbs 24a" on an opposite side of the implant 14a.

The interrupted barbs 24a', 24a" secure the implant within the bone portions. Particularly, the implant 14a has a first portion 26a and a second portion 28a, each of which has barbs 24a', 24a" on opposing sides thereof. It should be noted that the terms "first" and "second" portion as used in connection with the implant and bones are designated for descriptive purposes only and shall not be read as limiting. Accordingly, for instance, the terms the "first" and "second" portions of the implant are used interchangeably, unless indicated otherwise. The first and second portions 26a, 28a are separated by an intermediate portion 30a. In at least one embodiment, the intermediate portion 30a does not have barbs 24a', 24a".

Additionally, in one embodiment the first portion 26a is relatively shorter than second portion 28a. Hence, as further described below, in some instances, the second portion 28a (i.e., the longer portion) is inserted into the proximal phalanx, while the first portion 26a (i.e., the shorter portion) is inserted into the middle phalanx. Those skilled in the art should appreciate that the proximal phalanx is typically longer than the middle phalanx and, consequently, can accommodate a longer portion of the implant 14a. Furthermore, a typical middle phalanx has a larger cross-section than the proximal phalanx, which can accommodate the first portion 26a that has a larger cross-section than the second portion 28a. Hence, in some embodiments, the first portion 26a of the implant 14a has a bigger cross-section than the second portion 28a. In other embodiments, however, as further described below, the second portion 28a can have a larger cross-section than the first portion 26. Also, the first portion 26a can be relatively longer than the second portion 28a.

In other embodiments, the implant 14a can have other configurations. For instance, the implant 14a can have uninterrupted barbs, which can encircle the implant 14a. The implant 14a also can have any number of barbs on either the first portion 26a, the second portion 28a, the intermediate portion 30a, and combination thereof. Furthermore, the barbs can have any number of shapes suitable for securing the implant 14a within bone. Moreover, in one or more embodiments, in lieu of or in addition to the barbs 24a', 24a", the implant 14a can have one or more press-fit sections on the first and/or the second portions 26a, 28a, which can be press fitted into bone portions (e.g., the press-fit section of the implant 14a can form an interference fit within holes in the bone portions).

The intermediate portion 30a can accept and removably secure the spacer 16a. Particularly, a slot 32a can fit over and couple to the intermediate portion 30a. In the illustrated embodiment, the slot 32a has a substantially rectangular shape which fits over a corresponding, substantially rectangular shape of the intermediate portion 30a. Additionally, the spacer 16a can have a snug or firm fit with the implant 14a. For example, in at least one embodiment, the spacer 16a has dimples 34a, which form an interference fit with the intermediate portion 30a, thereby firmly securing the spacer 16a to the intermediate portion 30a of the implant 14a. Such snug or firm fit between the spacer 16a and the implant 14a can allow the spacer 16a to remain on the implant 14a while the implant 14a is inserted into the bone portions.

Additionally, the spacer 16a has a grip section 36a, which can provide better grip for the user. Particularly, the grip section 36a has multiple serrations, which create an increased surface area of contact between the user's hand and the spacer 16a, thereby providing a better grip for the user. Hence, the user can secure the spacer 16a to the implant 14a more easily. Similarly, the grip section 36a also can allow the user to remove the spacer 16a from the implant 14a more easily.

In other embodiments, the slot 32a of the spacer 16a and/or the intermediate portion 30a of the implant 14a can have any number of shapes and sizes. For example, the intermediate portion 30a can have arcuate sidewalls. Similarly, the spacer 16a also can have at least partially arcuate sidewalls forming the slot 32a. Accordingly, the spacer 16a can snap onto the intermediate portion 30a of the implant 14a. In other words, as the slot 32a is fitted over the intermediate portion 30a, the arcuate sidewalls forming the slot 32a can deflect around the intermediate portion 30a and, subsequently, return to their original position when the slot 32a reaches its final location with respect to the intermediate section 30a of the implant 14a. In light of this disclosure, other configurations of the slot 32a and the intermediate portion 30a, which can allow the spacer 16a to be secured to the implant 14a should be apparent to those skilled in the art.

Thus, when secured to the implant 14a, the spacer 16a can ensure proper depth positioning of the first and second portions 26a, 28a of the implant 14a within the bone portions. Additionally or alternatively, the spacer 16a can help the user to orient the implant 14a with respect to the bone portion. For instance, in at least one embodiment, the spacer 16a is positioned substantially orthogonally with respect to the implant 14a. Accordingly, the user can orient the implant 14a by orienting the spacer 16a, which is more visible and can aid the user with properly orienting the implant 14a before and during insertion thereof into the bone portion.

As noted above, the handle 12a can secure the implant 14a within the hole 22a, such that the user can insert the second portion 28a of the implant 14a into a first bone portion (further described below). Accordingly, the hole 22a has a suitable shape and size that can at least partially accommodate the first portion 26a of the implant 14a. Similarly, the implant 14a has a cross-section with a corresponding shape that fits into the hole 22a. For example, in some embodiments, the handle 12a has a rectangular shaped hole 22a, and the implant 14a has a cross-section that allows the implant 14a to fit into the rectangular shaped hole 22a. As mentioned above, in some embodiments, the lengths and/or width of the first and second portions 26a, 28a can be different from each other. Hence, the size and shape of the hole 22a can be such that accommodates a particular size and shape of the first portion 26a of the implant 14a.

Furthermore, the hole 22a can have a clearance between the walls thereof and the implant 14a, such that the implant 14a is loosely secured within the hole 22a. Alternatively, the hole 22a can form a snug or press (i.e., interference) fit with the implant 14a. In any event, the hole 22a can hold and locate the implant 14a in a predetermined orientation.

In other embodiments, the hole 22a can have any number of other shapes, including shapes that also can orient the implant 14a with respect to the handle 12a (e.g., by preventing the implant 14a from rotating within the hole 22a). For instance, the hole 22a can have an oval shape that can correspond with the cross-section of and secure the implant 14a in the handle 12a, such that the implant 14a is substantially prevented from rotating within the hole 22a. Additionally or alternatively, as noted above, the hole 22a and the implant 14a can form a snug or press fit. Accordingly, a tight fit between the hole 22a and the implant 14a also can prevent the implant 14a from rotating within the hole 22a (and the user can position the implant 14a within the hole 22a at a desired orientation). Preventing the implant 14a from rotating with respect to the handle 12a can help the user to correctly orient and implant the implant 14a within the bone portions. In other words, the implant 14a can have a predetermined orientation with respect to the handle 12a, such that the user holding the handle 12a can properly orient the implant 14a, to a desired orientation with respect to the bone portion.

Additionally, as noted above, at least a portion of the first portion 26a fits within the hole 22a. Hence, in some embodiments, the entire first portion 26a fits within the hole 22a. In other embodiments, however, some of the first portion 26a remains outside of the handle 12a. Moreover, in still further embodiments, at least a portion of the intermediate portion 30a also fits within the hole 22a. Thus, for example, the implant 14a can be inserted into the bone portion without having the spacer 16a secured thereto.

More specifically, when the entire intermediate portion 30a is contained within the hole 22a of the handle 12a, the distal portion 20a of the handle 12a can act as a stop (similar to the spacer 16a) and can prevent insertion of the implant 14a into the bone portion beyond the second portion 28a. In other words, when the second portion 28a is inserted into the bone portion, the distal portion 20a of the handle 12a abuts the bone portion, thereby preventing further insertion of the implant 14a into the bone portion.

In one or more embodiments, the proximal portion 18a of the handle 12a is shaped to facilitate grasping by a user. Such shape can be ergonomically designed to fit in a user's hand. In the illustrated embodiment, the proximal portion 18a of the handle 12a has a substantially oval shape and is sized to permit grasping thereof by the user. Additionally, the proximal portion 18a of the handle 12a has at least one orientation surface 38a. More specifically, the orientation surface 38a forms a substantially flat surface that spans across a large part of the proximal portion 18a.

In the illustrated embodiment, the orientation surface 38a is aligned with at least one wall of the hole 22a, which is, in turn, aligned with a flat land 40a on the implant 14a. Consequently, the orientation surface 38a is also aligned with the flat land 40a of the implant 14a. Thus, the user grasping the handle 12a can use the orientation surface 38a to orient the flat land 40a and, therefore, the implant 14a with respect to the bone portion receiving the first or the second portion 26a, 28a of the implant 14a.

In one or more other embodiments, the handle 12a can have other shapes and/or features, including features that can help the user to orient the implant 14a. For instance, the handle 12a can be substantially round (e.g., can have a cylindrical shape). Similarly, features enabling the user to determine the orientation of the implant 14a within the handle 12a can vary from one embodiment to another. For example, the handle 12a can include a line or another marker that indicates location of the flat land 40a.

Similarly, in addition to or in lieu of the flat land 40a, the implant 14a can include other physical or printed landmarks (visible on the implant 14a) for aligning the implant 14a within the handle 12a. For instance, the implant 14a can include lines, dots, or other symbols imprinted thereon, which can be aligned with a predetermined location (or locations) on the distal portion 20a of the handle 12a. Examples of physical landmarks include dimples, protrusions, and slots. Particularly, the handle also can include a divider that can fit into a slot of the implant, thereby orienting the implant with respect to the handle.

Figure 1B:
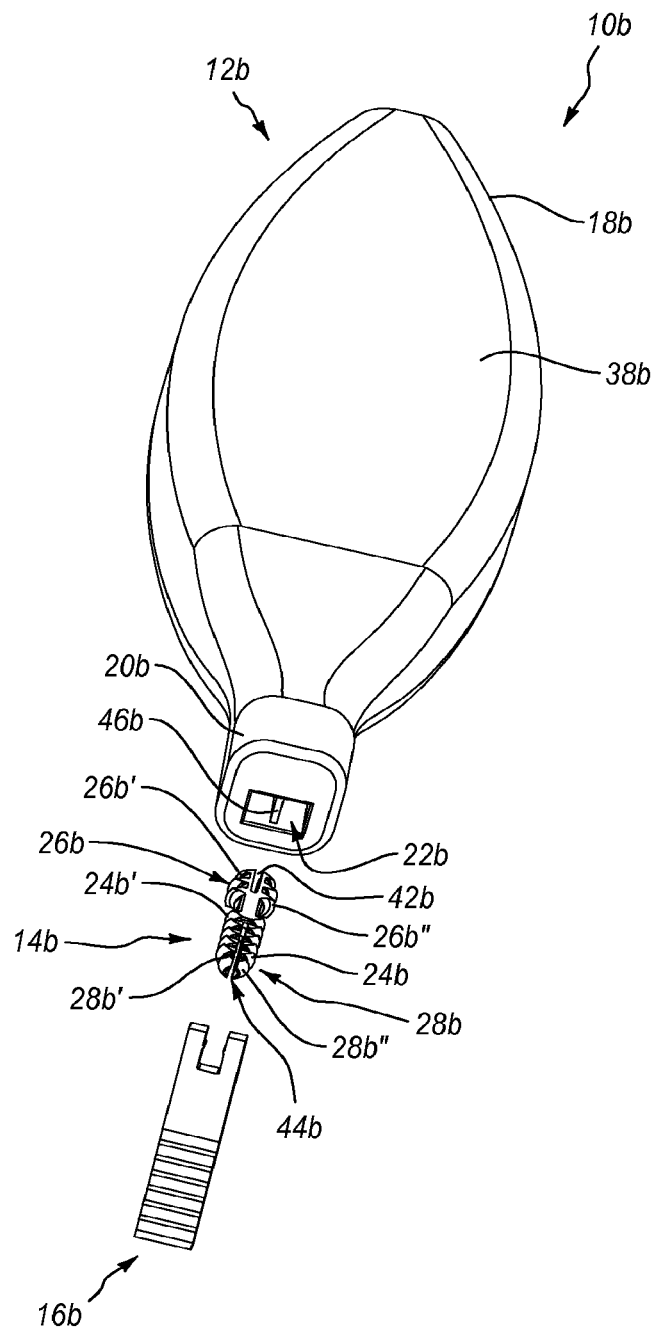
FIG. 1B illustrates a perspective view of an implant system in accordance with another embodiment of the present invention.

For example, as shown in the embodiment illustrated in FIG. 1B, an implant system 10b includes a handle 12b, an implant 14b, and a spacer 16b. The handle 12b, implant 14b, and spacer 16b can be substantially the same as the handle 12a, implant 14a, and spacer 16a (FIG. 1A), respectively. Additionally or alternatively (as applicable), however, the handle 12b and the implant 14b have other features as further described below. More specifically, for instance, the implant 14b includes slots 42b, 44b.

The slot 42b is located in a first portion 26b of the implant 14b, and divides the first portion 26b into sections 26b' and 26b". Similarly, the slot 44b is located in a second portion 28b of the implant 14b and divides the second portion 28b into sections 28b' and 28b". Hence, the slots 42b, 44b can allow the respective sections 26b', 26b", 28b', 28b" to flex or collapse together into a narrower configuration and to spring back to their original configuration. In other words, for example, as the second portion 28b of the implant 14b is inserted into a hole made in the bone portion, the sections 28b', 28b" can collapse to fit into the hole and spring back to their original positions to engage barbs 24b' with the hole in the bone portion.

Additionally or alternatively, as noted above, the slot 42b can help to align the implant 14b with the handle 12b. Particularly, the handle 12b includes a hole 22b in a distal portion 20b, and the hole 22b includes a divider 46b. Furthermore, the handle 12b includes a proximal portion 18b that has an orientation surface 38b. The orientation surface 38b has a predetermined position or orientation with respect to the divider 46b. In the illustrated embodiment, the orientation surface 38b is positioned orthogonally with respect to the divider 46b.

The divider 46b is configured to fit into the slot 42b (and vice versa). Accordingly, after inserting the implant 14b into the hole 22b, the slot 42b and, consequently, the implant 14b will have a predetermined orientation with respect to the orientation surface 38b. Hence, the user can utilize the orientation surface 38b to position the implant 14b in a desired orientation with respect to the bone portion receiving the implant 14b.

Furthermore, the divider 46b permits relaxed dimensional tolerances for the hole 22b. Specifically, because the implant 14b is oriented by positioning the divider 46b within the slot 42b, the shape and dimensions of the hole 22b does not have to closely correspond with the cross-section of the implant 14b in order to prevent the implant 14b from rotating. Accordingly, the hole 22b can have greater clearance between the walls thereof and the implant 14b, as compared with a hole that does not have a divider that fits into a slot of an implant.

It should be noted, however, that excessive clearance between the implant 14b and the walls of the hole 22b can interfere with proper placement of the implant 14b in the bone portion, as such clearance may allow the implant 14b to move about the divider 46b (e.g., in an orthogonal direction with respect to the opening 22b). Thus, in at least one embodiment, the hole 22b is configured to hold the implant 14b such that the implant 14b has limited amount movement within the hole 22b. For example, the hole 22b can have 0.005" of clearance per side with respect to the implant 14b (i.e., 0.005" gap between each of the walls of the hole 22b and the implant 14b).

Figure 1C:
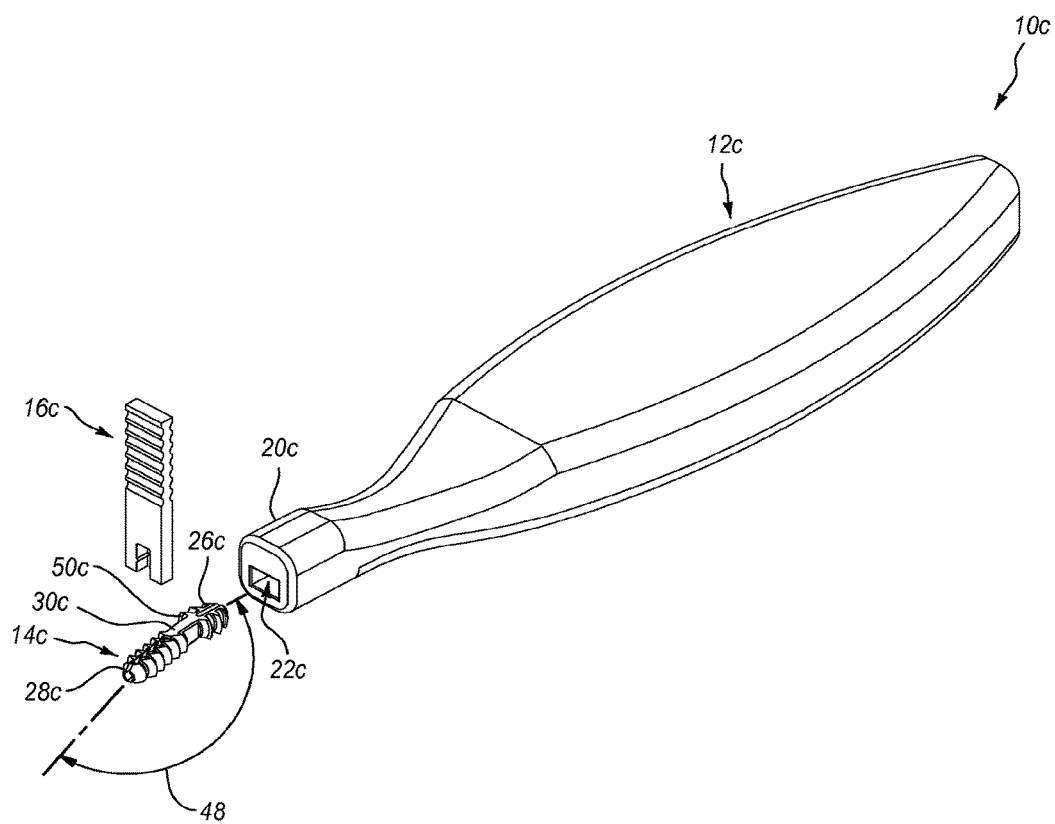
FIG. 1C illustrates a perspective view of an implant system in accordance with yet another embodiment of the present invention.

The above description relates to the implant systems that include linear implants 14a, 14b (see FIGS. 1A-1B). It is to be appreciated that this invention is not so limited. For example, as illustrated in FIG. 1C, embodiments of the present inventions include an implant system 10c that has non-linear implant configurations. In particular, the implant system 10c includes a handle 12c, an implant 14c, and a spacer 16c. In some embodiments, the implant system 10c does not include the spacer 16c. The handle 12c, implant 14c, and spacer 16c are substantially the same as the handle 12a, implant 14a, and spacer 16a (FIG. 1A), respectively, except as otherwise described below. For instance, the implant 14c has other features as further described below. More specifically, a first portion 26c and a second portion 28c form an angle 48 with respect to each other about a bend point 50c.

In one embodiment, the angle 48 is approximately 10 degrees. In light of this disclosure, it should be apparent to those skilled in the art that the angle between the first and second portions 26c, 28c can be greater or less than 10 degrees. Nevertheless, it is noted that some angles may be impractical in light of the particular application of the implant 14c. Accordingly, the angle 48 can be designed as best suited for a particular connection of bone portions.

Thus, the first and second portions 26c, 28c remain linear, but form an angle about the bend point 50c. In the illustrated embodiment, the bend point 50c is located at the transition point between the first portion 26c and an intermediate portion 30c. In other words, the second portion 28c and the intermediate portion 30c form a linear segment of the implant 14c and the first portion 26c forms another linear segment.

In other embodiments, the bend point 50 can be located anywhere between the first and second portions 26c, 28c. The bend point 50c also can be located at other points along the implant 14c. Furthermore, the implant 14c can have other non-linear configurations and may be curved along one or more axes. Similarly, the first and second portions 26c, 28c of the implant 14c can form compound angles with respect to each other—i.e., the first and second portions 26c, 28c can be angled with respect to each other along two or more axes. As further described and illustrated below, when connected with a non-linear implant (such as the implant 14c) two bone portions form a non-linear connection.

Because the implant 14c comprises two linear segments, which form an obtuse or acute angled therebetween, the implant 14c can fit into a straight hole 22c located in a distal portion of the handle 12c. Alternatively, the hole 22c can have other configurations, suitable to accept the particular non-linear implant 14c. For instance, the hole 22c can be linear and have sufficient clearance therein to accept non-linear sections of the implant 14c. In other embodiments, the hole 22c can have a non-linear geometry, which can accommodate a non-linear section (e.g., a non-linear first portion 26c) of the implant 14c.

Figure 1D:
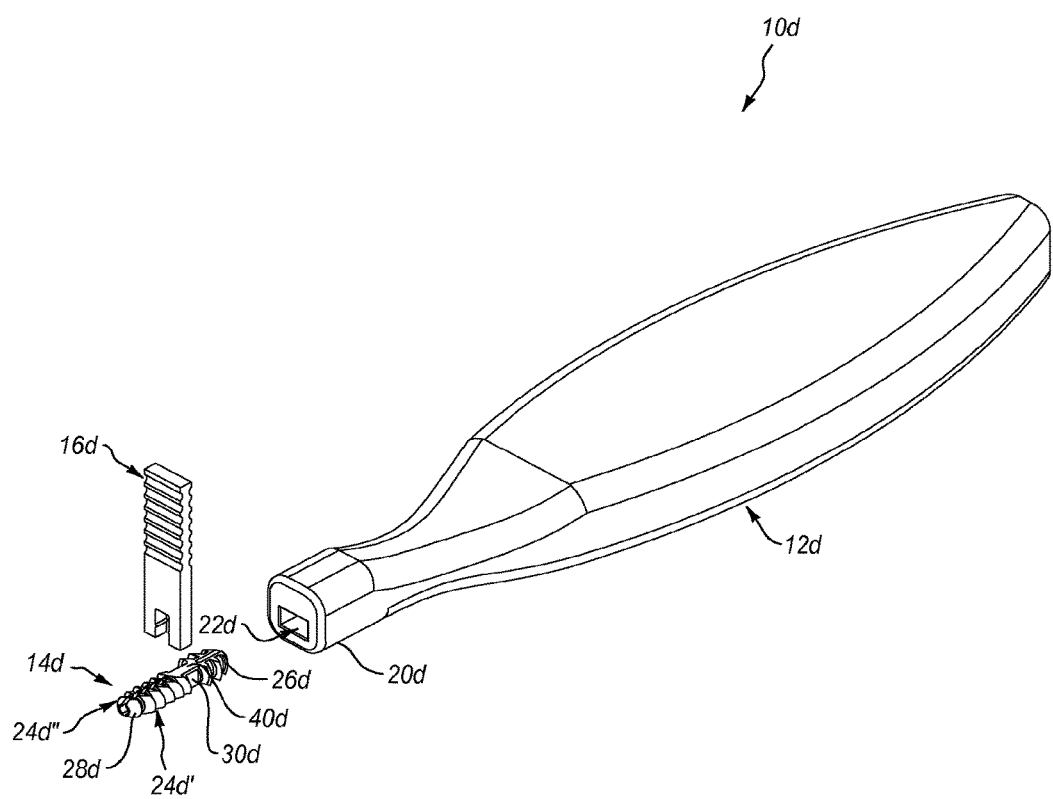
FIG. 1D illustrates a perspective view of an implant system in accordance with still one other embodiment of the present invention.

Additionally, one or more portions of the implant can have a threaded configuration. For example, as shown in the embodiment illustrated in FIG. 1D, an implant system 10d includes a handle 12d, an implant 14d, and a spacer 16d. The handle 12d, implant 14d, and spacer 16d can be substantially the same as the handle 12a, implant 14a, and spacer 16a (FIG. 1A), respectively. Additionally or alternatively (as applicable), however, the handle 12d and/or the implant 14d have other features as further described below.

For instance, similar to the implant 14a (FIG. 1A), the implant 14d has a first portion 26d (that has multiple barbs) and a second portion 28d, which is separated from the first portion 26d by an intermediate portion 30d. Also, the spacer 16d fits over the intermediate portion 30d (as described above in connection with the spacer 16, shown in FIG. 1A). Additionally, however, a second portion 28d of the implant 14d includes barbs 24d' and 24d" that can be threaded into a bone portion. In other words, the barbs 24d' and 24d" form an interrupted thread (similar to a thread of a screw). The implant 14d also can have a flat land 40d, which can help with gripping the implant 14d as well as holding the implant 14d during rotation, as the implant 14d is screwed into a bone portion.

In the illustrated embodiment, the implant 14d has a substantially linear configuration. It should be noted, however, that this invention is not so limited. For instance, the implant 14d can have angled configuration (e.g., similar to the implant 14d, shown in FIG. 1C) or other non-linear configurations. Additionally, the first and/or second portions 26d, 28d of the implant 14d can have slots (similar to the implant 14b, shown in FIG. 1B).

As described above, the first portion 26d of the implant 14d fits into a hole 22d, located in a distal portion 20d of the handle 12d. The hole 20d holds the implant 14d, such that the user can screw the second portion 28d into a bone portion (described below). Additionally, in some embodiments, the hole 20d can include a divider that can fit into a slot in the implant 14d and can further assist in preventing the implant 14d from rotating, when the second portion 28d is screwed into the bone portion. Furthermore, the hole 20d can be positioned at an angle with respect to a center axis of the handle 12d, such that, for instance, when an angled implant 14d is inserted into the hole 20d, the second portion 28d can be substantially aligned with the center axis of the handle 12d. In other words, rotating the handle 12d about the center axis thereof will, in turn, cause rotation of the second portion 28d about a center axis of the second portion 28d.

As described above, the implant system 10a, 10b, 10c, 10d can be used to connect and/or fuse two bone portions, and such connections can be substantially linear or non-linear. Particularly, the implant system 10a can be used to connect and/or reconnect a middle and proximal phalanges of a patient's foot. Thus, as illustrated in FIGS. 2-8, such procedure can be used, for example, to correct a condition known as hammer toe.

Figure 2:
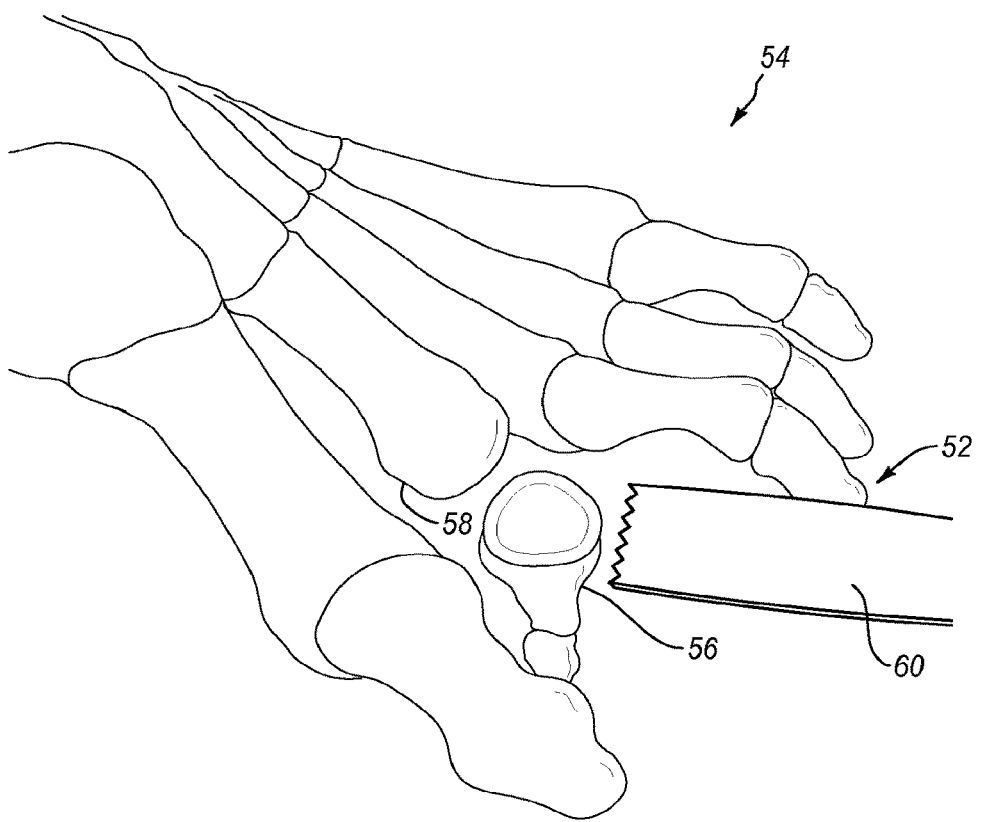
FIG. 2 illustrates a perspective view of a schematic representation of a step of a procedure for severing proximal and middle phalanges of a foot in accordance with one embodiment of the present invention.

Referring now to FIG. 2, in at least one embodiment, to correct the hammer toe condition, illustrated on phalanges 52 of a patient's foot 54, a middle phalanx 56 is first separated from a proximal phalanx 58 of a patient's foot 54. Hence, a joint connecting the middle phalanx 56 to the proximal phalanx 58 is initially exposed by making an appropriate incision in the patient's foot 54. Subsequently, a saw 60 (e.g., a reciprocating saw) is used to separate the middle phalanx 56 from the proximal phalanx 58. It should be noted that FIG. 2 provides a schematic representation of the above step in the procedure. During the procedure, the middle phalanx 56 and the proximal phalanx 58 remain connected with connective tissue, such as skin and tendons.

Figure 3:
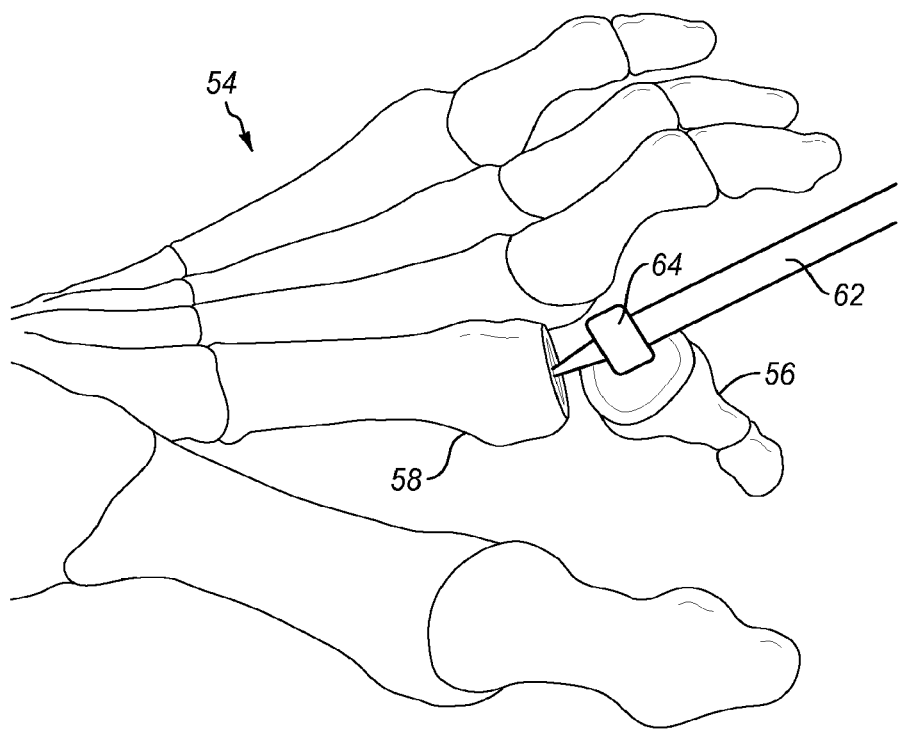
FIG. 3 illustrates a perspective view of a schematic representation of another step of a procedure for connecting proximal and middle phalanges of a foot with an implant in accordance with one embodiment of the present invention.

After separating the middle phalanx 56 from the proximal phalanx 58, a blind hole is made in the proximal phalanx 58, as illustrated in FIG. 3. A drill or a k-wire is used to make the blind hole in the proximal phalanx 58 of the patient's foot 54. In the illustrated embodiment, a drill 62 is used to make the blind hole in the proximal phalanx 58. Additionally, a stopper 64 is secured to the drill 62 to control the depth of penetration of the drill 62 into the proximal phalanx 58. Thus, the drill 62 can drill into the proximal phalanx 58 only up to the stopper 64, thereby creating a blind hole that has a depth approximately equal to the distance between the tip of the drill 62 and the stopper 64.

Figure 4:
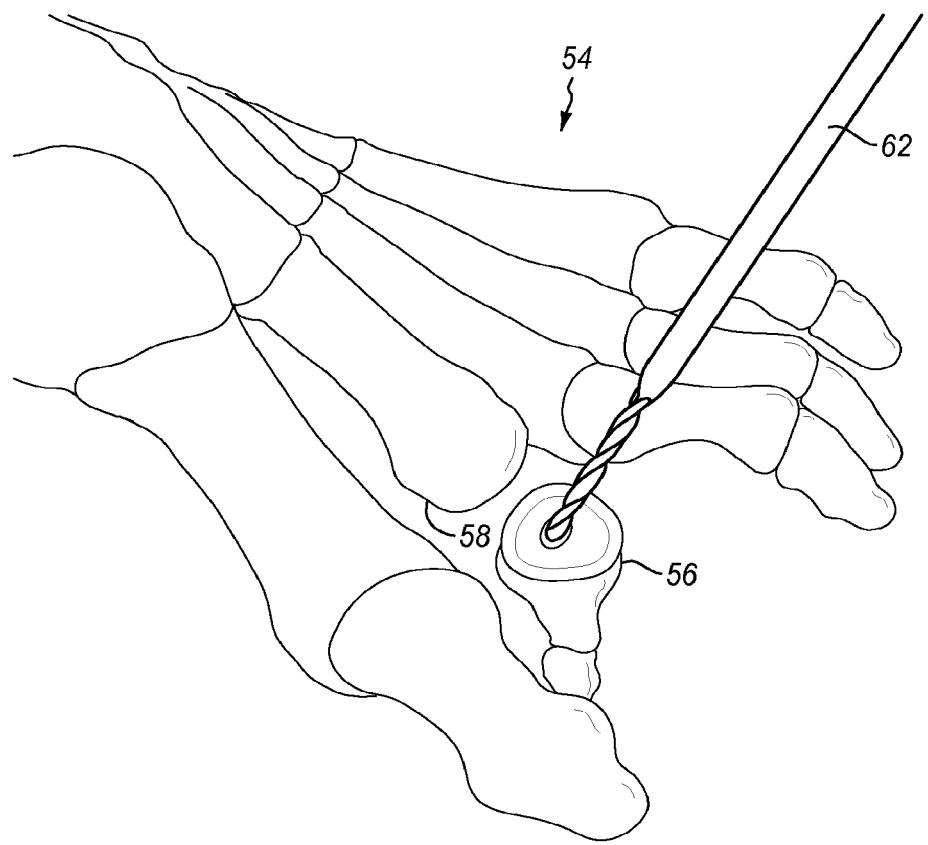
FIG. 4 illustrates a perspective view of a schematic representation of still another step of a procedure for connecting proximal and middle phalanges of a foot with an implant in accordance with one embodiment of the present invention.

In another step, schematically illustrated in FIG. 4, a hole also can be drilled in the middle phalanx 56 of the patient's foot 54. Particularly, the drill 62 is used to make the hole in the middle phalanx 56. In some embodiments, the hole drilled in the middle phalanx 56 is a blind hole. However, the depth of the hole in the middle phalanx 56 need not be controlled as closely as the depth of the hole located in the proximal phalanx 58. Accordingly, in at least one embodiment, the drill 62 is used without a stopper. Alternatively, however, a stopper can be used on the drill 62 during drilling of the hole in the middle phalanx 56, and such stopper may prevent over-drilling the hole in the middle phalanx 56.

Figure 5A:
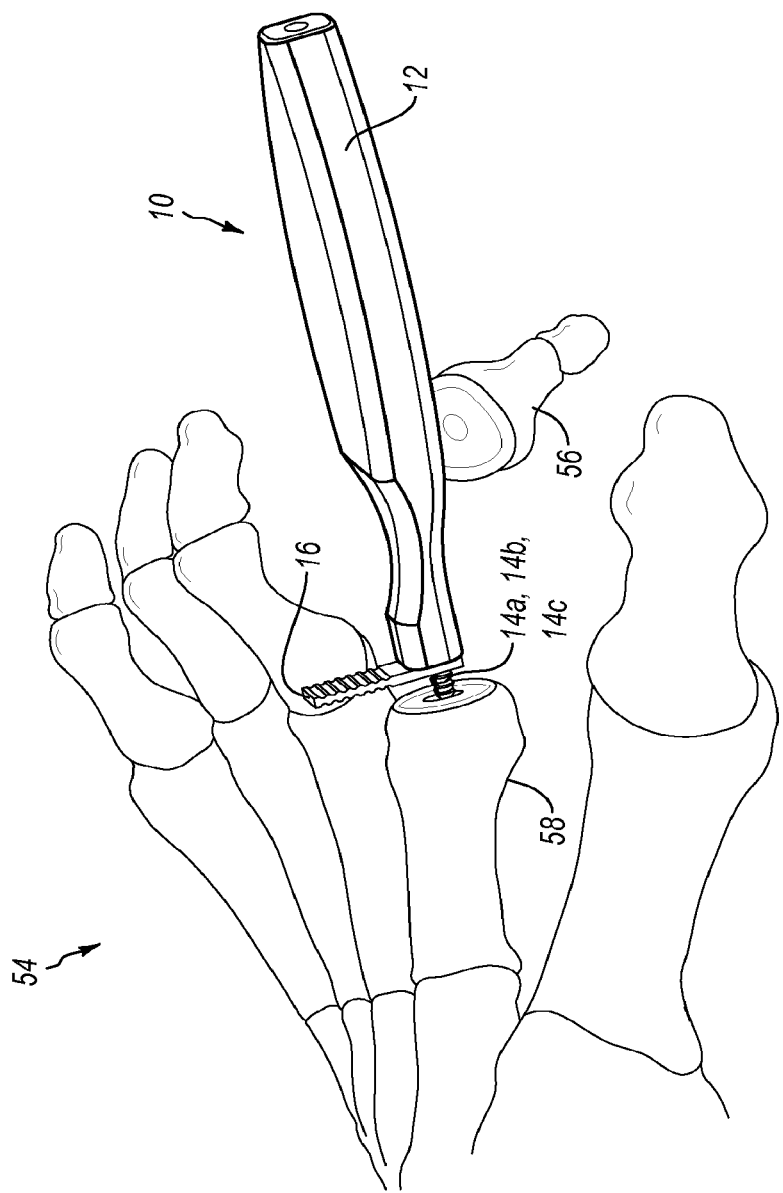
FIG. 5A illustrates a perspective view of a schematic representation of an implant insertion step of a procedure for connecting proximal and middle phalanges of a foot with an implant in accordance with one embodiment of the present invention.

In still another step, schematically illustrated in FIG. 5A, an implant system is used to insert an implant 14a, 14b, 14c into the proximal phalanx 58. Particularly, the implant 14a, 14b, 14c is held in a handle 12, as described above in connection with FIGS. 1A-1D. The handle 12 is used to insert the implant 14a, 14b, 14c into the hole previously drilled in the proximal phalanx 58. A spacer 16 acts as a stop, preventing insertion of the implant 14a, 14b, 14c into the proximal phalanx 58 beyond a predetermined depth. More specifically, the spacer 16 prevents insertion of the implant 14a, 14b, 14c into the proximal phalanx 58 beyond a length of a second portion of the implant 14a, 14b, 14c.

In alternative implementations the implant can be inserted into the middle phalanx 56, before inserting the implant 14a, 14b, 14c into the proximal phalanx 58. Furthermore, as described above, the insertion of the implant 14a, 14b, 14c into the bone portion (e.g., middle or proximal phalanx 56, 58) can be performed without using the spacer 16. For instance, when the first and intermediate portions are located within the hole of the handle, the distal portion of the handle will abut the proximal phalanx 58, thereby controlling and/or limiting the depth of insertion of the implant 14a, 14b, 14c.

After inserting the implant 14a, 14b, 14c into the proximal phalanx 58, the handle 12 is removed from the inserted implant 14a, 14b, 14c. As noted above, in some embodiments, the handle 12 is disposable. Consequently, after removing the handle 12 from the implant 14a, 14b, 14c, the handle 12 can be discarded. Although the handle 12 is removed from the implant 14a, 14b, 14c, the spacer 16 remains secured to the implant 14a, 14b, 14c.

Figure 5B:
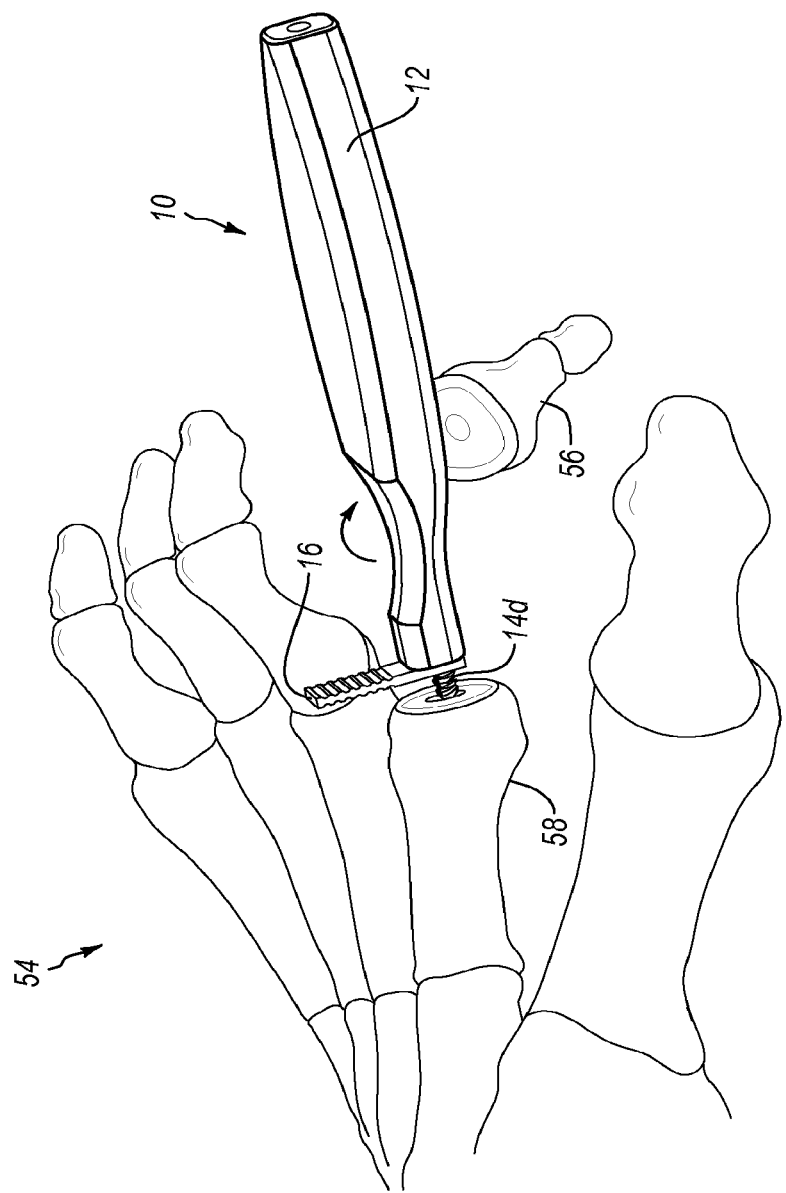
FIG. 5B illustrates a perspective view of a schematic representation of an implant insertion step of a procedure for connecting proximal and middle phalanges of a foot with an implant in accordance with another embodiment of the present invention.

Alternatively, as illustrated in FIG. 5B, in one or more embodiments, the implant 14d is screwed into the proximal phalanx 58. In the illustrated embodiment, the second portion of the implant 14d has barbs that form a thread, which can be screwed into the proximal phalanx 58. In at least one embodiment, the barbs form a right-handed thread on the implant 14d. Accordingly, the handle 12 together with the implant 14d are rotated clockwise, to screw the implant 14d into the proximal phalanx 58. In other embodiments, however, the implant 14d can have a left-handed thread, and the handle 12 can be rotated counterclockwise, to screw the implant 14d into the proximal phalanx 58. Furthermore, as the handle 12 rotates, to advance the implant 14d into the proximal phalanx 58, the spacer 16 can either rotate together with the implant 14d or can remain stationary (i.e., the implant 14d can rotate inside of the spacer 16).

Figure 6:
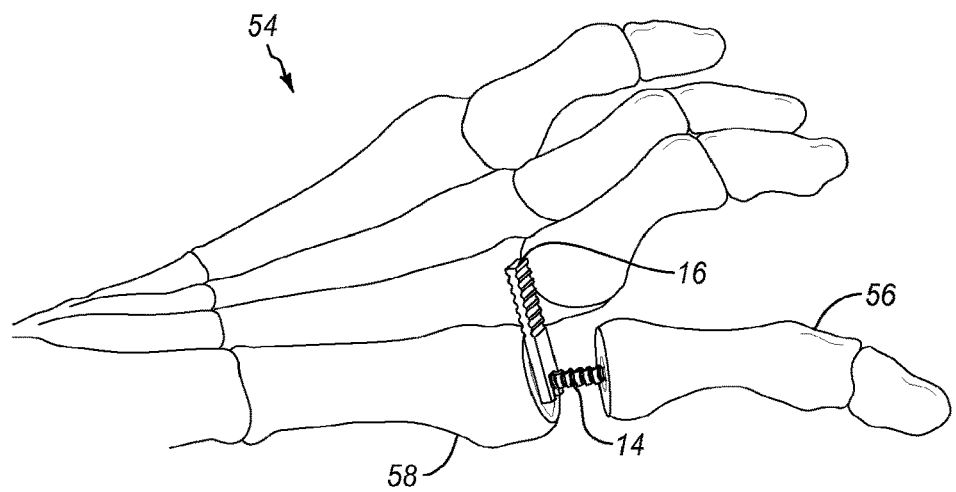
FIG. 6 illustrates a perspective view of a schematic representation of another implant insertion step of a procedure for connecting proximal and middle phalanges of a foot with an implant in accordance with one embodiment of the present invention.

Thereafter, the handle 12 is removed from the implant 14 (e.g., from the first portion of any one of the implants 14a, 14b, 14c, 14e (see Figured 1A-1D)), and the middle phalanx 56 is inserted onto the implant 14, as schematically illustrated in FIG. 6. Namely, the hole previously drilled in the middle phalanx 56 is fitted over the implant 14. Thereafter, the middle phalanx 56 is pushed toward the proximal phalanx 58, such that both the middle phalanx 56 and the proximal phalanx 58 abut the spacer 16 on opposing sides thereof, as illustrated in FIGS. 7A-7B.

Figure 7A:
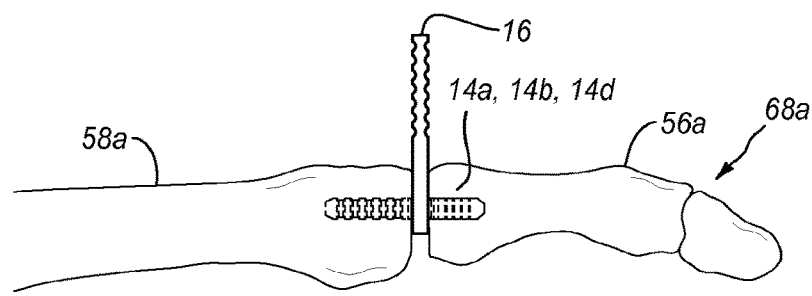
FIG. 7A illustrates a side view of a schematic representation of a linearly connected proximal and middle phalanges before removal of a spacer from the connection in accordance with one embodiment of the present invention.

Particularly, FIG. 7A schematically illustrates an incomplete linear connection between proximal phalanx 54a and the proximal phalanx 58a. As described above, such connection is made using a linear implant, for example, implant 14a, 14b, 14d (FIGS. 1A-1D). By contrast, FIG. 7B schematically illustrates a non-linear connection made between middle phalanx 56b and proximal phalanx 58b. The non-linear connection is made using a non-linear implant, for example, implant 14c, 14d (where the implant 14d is angled).

Figure 7B:
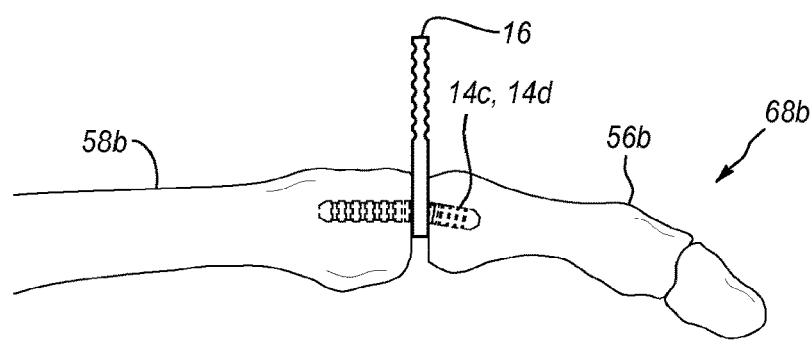
FIG. 7B illustrates a side view of a schematic representation of a non-linearly connected proximal and middle phalanges before removal of a spacer from the connection in accordance with another embodiment of the present invention.

In both instances, the spacer 16 initially remains between the middle phalanx 56a, 56b and the proximal phalanx 58a, 58b, to ensure that the respective first and second portions of the implant 14a, 14b, 14c, 14d (as applicable) remain in appropriate bone portions (FIGS. 7A-7B). In other words, the spacer 16 ensures that the first portion of the implant 14a, 14b, 14c, 14d is inserted in the middle phalanx 56a, 56b. Similarly, the spacer 16 also ensures that the second portion of the implant 14a, 14b, 14c, 14d is inserted in the proximal phalanx 58a, 58b.

A linearly connected middle phalanx 56a and proximal phalanx 58a can form a corrected toe 68a that points substantially straight and outward (FIG. 7A). In contrast to the linear connections, in the non-linear connection between the middle phalanx 54b and the proximal phalanx 58b, a corrected toe 68b points downward (FIG. 7B). In some instance, depending on the patient's foot, a downward pointing corrected toe (e.g., corrected toe 68b) creates a more natural toe position. Accordingly, depending on the patient's foot, a linear implant, a non-linear implant, or a combination thereof can be used to ensure proper position and orientations of the patient's toes.

Figure 8:
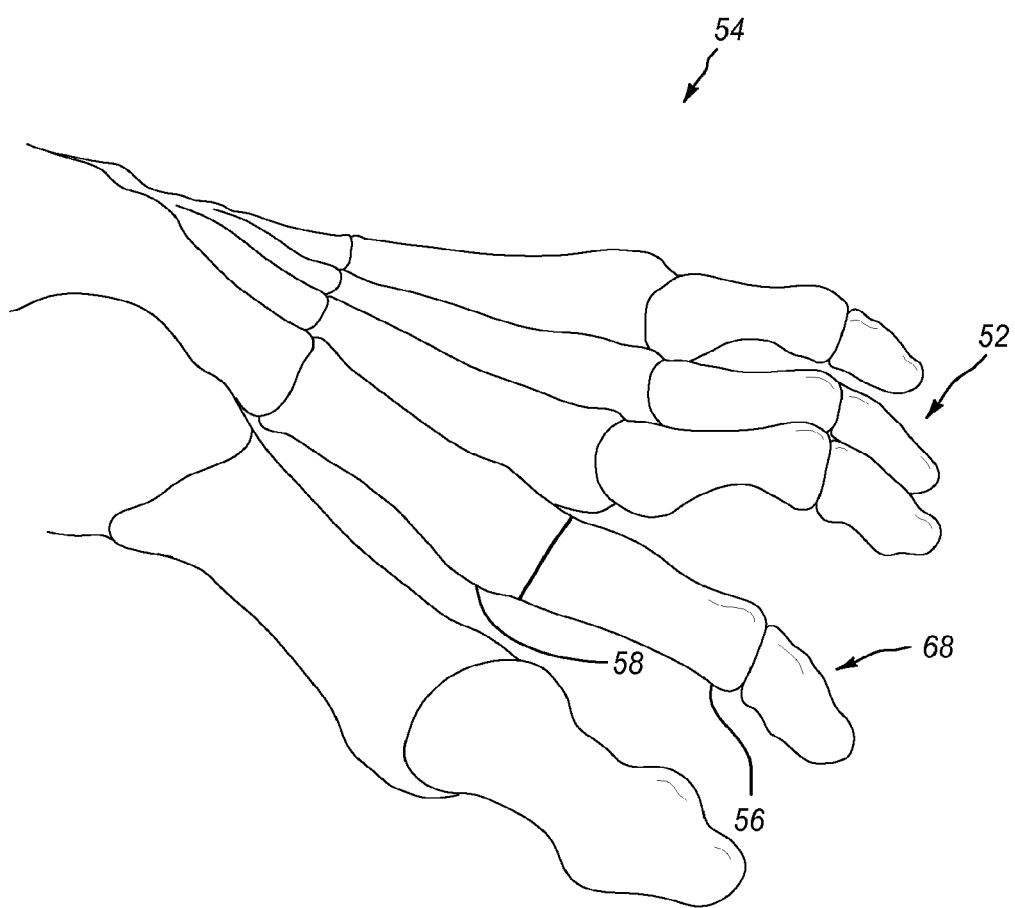
FIG. 8 illustrates a perspective view of a schematic representation of a foot after completion of a procedure for connecting proximal and middle phalanges of the foot in accordance with one embodiment of the present invention.

Subsequently, the spacer 16 is removed and the middle phalanx 56 and proximal phalanx 58 are further pushed closer together, thereby closing the gap previously occupied by the spacer 16 and forming a corrected toe 68, as illustrated in FIG. 8. FIG. 8 also schematically illustrates the difference between the corrected toe 68 and toes 52 afflicted with the hammer toe condition. Particularly, FIG. 8 illustrates linearly connected middle phalanx 56 and proximal phalanx 58, forming the corrected toe 68.

Figure 9:
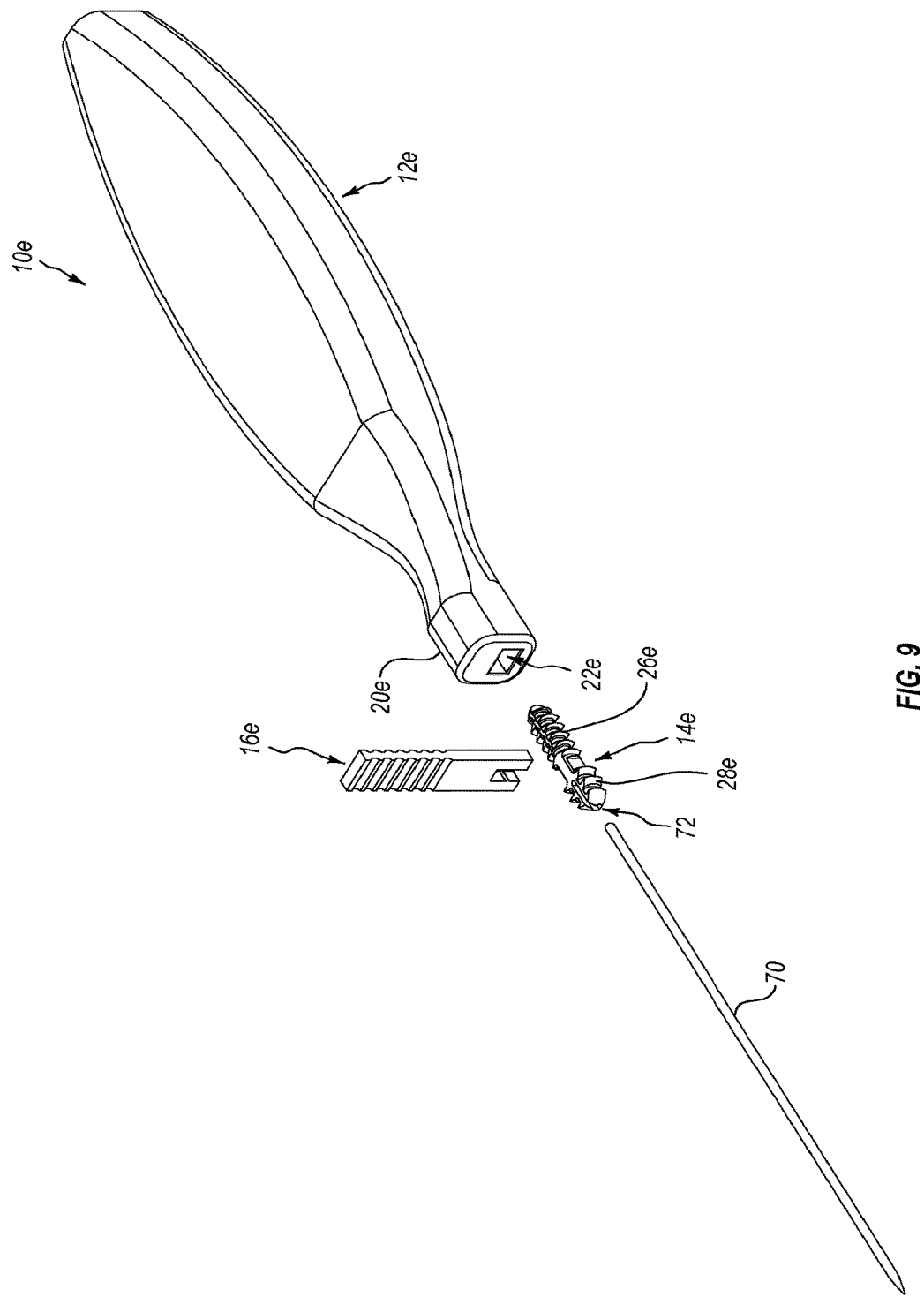
FIG. 9 illustrates a perspective view of an implant system in accordance with still one other embodiment of the present invention.

In the above described embodiments, the implant system includes a handle, an implant, a spacer, and/or combinations thereof. However, this invention is not so limited. In at least one embodiment, the implant system includes additional components. For example, as illustrated in FIG. 9, an implant system 10e includes a handle 12e, an implant 14e, a spacer 16e, and a k-wire 70. The handle 12e, implant 14e, and spacer 16e can be substantially the same as the handle 12a, implant 14a, and spacer 16a (FIG. 1A), respectively, except as otherwise described below. Particularly, the handle 12e and the implant 14e have certain features that distinguish the handle 12e and the implant 14e from the handle 12a and implant 14a (FIG. 1A). For example, the implant 14e includes a passageway 72 therethrough.

Similar to the implant 14a (FIG. 1A), the implant 14e has a first portion 26e and a second portion 28e. In at least one embodiment, the first portion 26e is relatively longer than the second portion 28e. Furthermore, the first portion 26e has a smaller cross-section than the second portion 28e. Accordingly, in some embodiments, as noted above, the second portion 28e (i.e., the shorter portion) is inserted into the middle phalanx, and the first portion 26e (i.e., the longer portion) is inserted into the proximal phalanx. In other embodiments, (e.g., as described above) the implant 14e can have the first and second portions 26e, 28e that have any number of other dimensional relationships with respect to each other.

The passageway 72 accommodates the k-wire 70, which has a cylindrical shape, and allows the k-wire 70 to pass therethrough. The passageway 72 is substantially round and has a slight clearance for the k-wire 70 to pass, such that the k-wire 70 can provide location for the implant 14e, as the implant 14e slides over the k-wire 70. For example, the passageway 72 can have a total of 0.004" (i.e., 0.002" per side) clearance with respect to the k-wire 70. In other words, an outside diameter of the k-wire 70 can be 0.004" smaller than an inside diameter of the passageway 72.

In other embodiments, the k-wire 70 and/or the passageway 72 can have other shapes and configurations. For instance, at least a part of the k-wire 70 and/or the passageway 72 can have a polygonal shaped cross-section, such as a rectangular cross-section. Such cross-section also can aid in properly orienting the implant 14e with respect to the bone portions being connected thereby. Furthermore, in some embodiments, the passageway 72 can have a greater or lesser clearance than 0.004" with the k-wire 70.

Moreover, in the illustrated embodiment, the passageway 72 is positioned along a centerline of the implant 14e. However, it is to be appreciated that this invention is not so limited. Hence, the passageway 72 can be located off center (i.e., not aligned with the centerline of the implant 14e).

Additionally, the handle 12e is configured to accommodate the k-wire 70. In particular, during the installation (i.e., insertion) of the implant 14e, the implant 14e is guided over the k-wire 70. While the implant 14e is guided over the k-wire 70, the implant 14e is held in the handle 12e (as described above in connection with the implant system 10a of FIG. 1A). Accordingly, in some embodiments, at least a portion of the k-wire 70 enters the handle 12e during the installation.

Furthermore, a hole 22e (located in a distal portion 20e of the implant 14e), can have an opening sized to accept the k-wire 70. More specifically, the opening can have a similar clearance between the walls thereof and the k-wire 70 as described above in connection with the passageway 72. Thus, the opening can locate or align the handle 12e with respect to the k-wire 70, thereby providing an additional guide for moving the handle 12e (together with the implant 14e) into a desired position (i.e., into a bone portion). Similar to the hole 22a (FIG. 1A), the hole 22e is sized and shaped such as to accept at least a part of the first portion 26e of the implant 14e.

The method of connecting and/or reconnecting bone portions described above in connection with FIGS. 2-9 relates to linear and non-linear connections made using an implant without a k-wire. This invention, however, is not so limited. For example, as illustrated in FIGS. 10A-15, procedure of connecting two bone portions (e.g., bone portions opposing a joint) with the implant can include insertion of a k-wire into one or both bone portions. Particularly, FIGS. 10A-15 schematically illustrate steps of a procedure for correction of the hammer toe condition in the patient's foot 54, after the middle phalanx 56 and the proximal phalanx 58 have been detached one from another (the detachment is illustrated in FIG. 2 and described in corresponding text above). In other words, the following description relates to reconnecting the middle phalanx 56 and the proximal phalanx 58 using the implant, such as the implant 14e (FIG. 9).

Figure 10A:
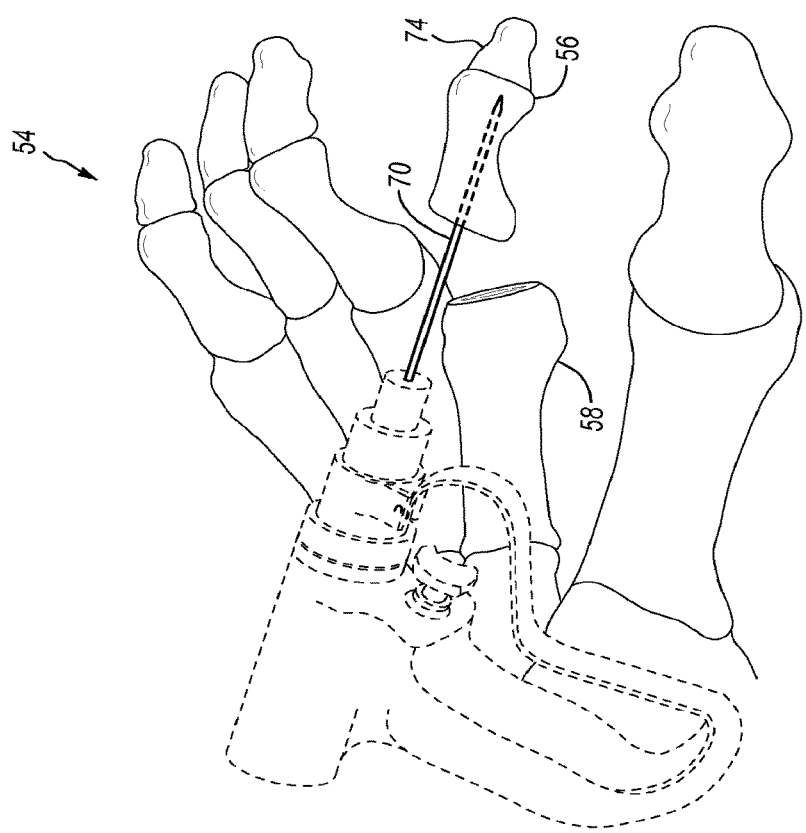
FIG. 10A illustrates a perspective view of a schematic representation of a step of a procedure for connecting proximal and middle phalanges of a foot with an implant in accordance with another embodiment of the present invention.
Figure 10B:
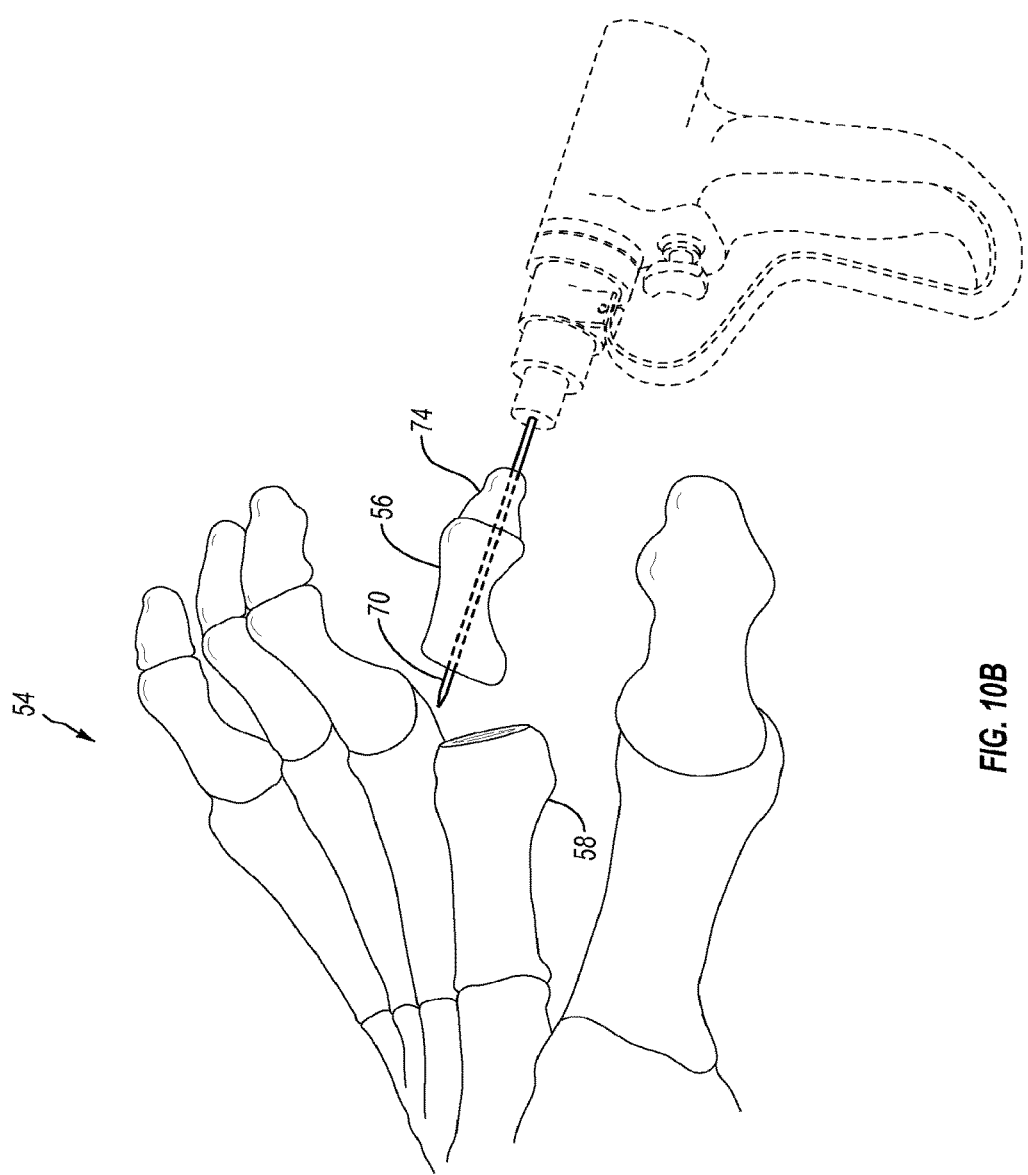
FIG. 10B illustrates a perspective view of a schematic representation of a step of a procedure for connecting proximal and middle phalanges of a foot with an implant in accordance with yet one other embodiment of the present invention.

Referring now to FIG. 10A, in one embodiment, the k-wire 70 is driven into the middle phalanx 56. More specifically, the k-wire 70 is driven into the middle phalanx 56 from the joint side of the middle phalanx 56 (i.e., at the partition between the middle phalanx 56 and the proximal phalanx 58). Alternatively, the k-wire 70 may be driven through the middle phalanx 56 from the side of a distal phalanx 74, as schematically illustrated in FIG. 10B. Hence, in at least one embodiment, the k-wire 70 passes through the middle phalanx 56 and comes out of the distal phalanx 74.

Figure 11:
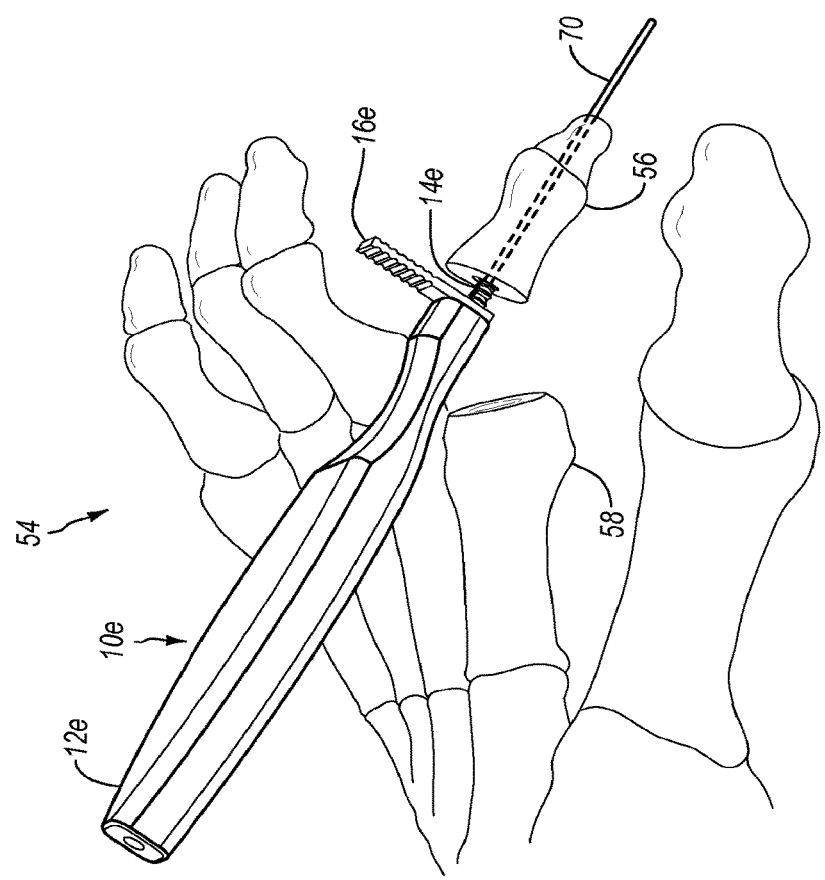
FIG. 11 illustrates a perspective view of a schematic representation of an implant insertion step of a procedure for connecting proximal and middle phalanges of a foot with an implant in accordance with one or more embodiments of the present invention.

After the k-wire 70 is driven through the middle phalanx 56 and, in some instances, through the distal phalanx 74 of the foot 54, the implant 14e is guided over the k-wire 70 into position, as schematically illustrated in FIG. 11. In some embodiments, the same k-wire can remain in the middle phalanx 56 and in the distal phalanx 74 as the k-wire that was used to penetrate the middle phalanx 56 and the distal phalanx 74. In alternative embodiments, a k-wire of a smaller diameter (than the k-wire used for penetration) is inserted after removing the k-wire that was used for penetrating the middle phalanx 56 and the distal phalanx 74. In any event, at least one k-wire 70 remains within the middle phalanx 56 and the implant 14e is guided over the k-wire 70 into an appropriate position.

More specifically, the implant system 10e is used to reconnect the middle phalanx 56 and the proximal phalanx 58 of the foot 54. The handle 12e holds the implant 14e, which has the spacer 16e secured thereto. The handle 12e is used to guide the implant 14e over the k-wire 70 and into the middle phalanx 56. In one embodiment, the second portion of the implant 14e fits into a recess or hole formed by or around the k-wire 70. Similar to the procedure described above in connection with FIGS. 2-8, the spacer 16e can be omitted during insertion of the implant 14e into the middle phalanx 56.

Figure 12:
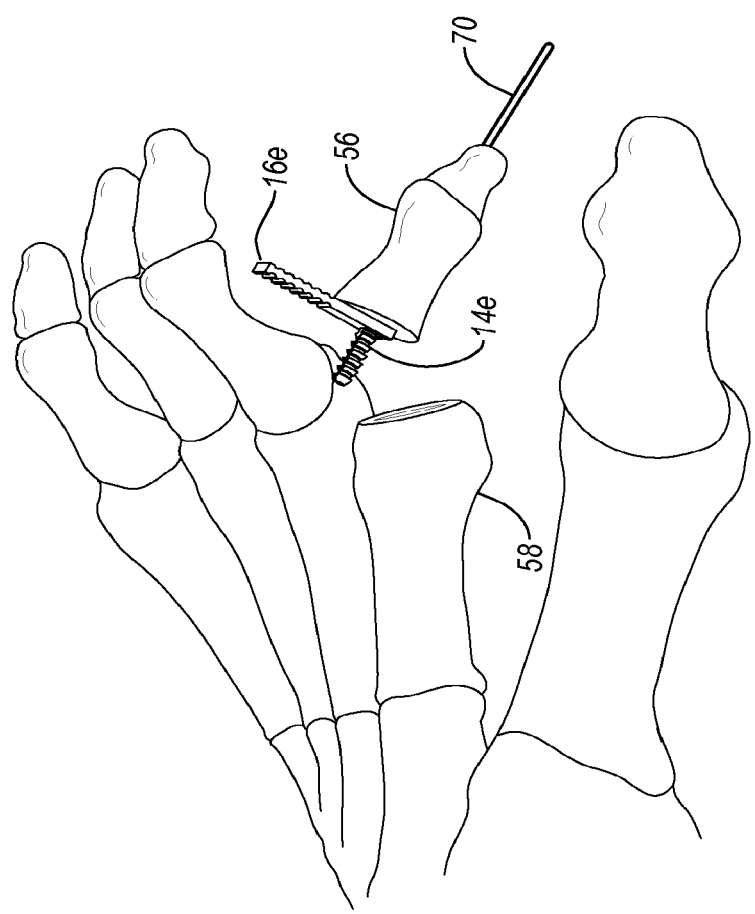
FIG. 12 illustrates a perspective view of a schematic representation of another implant insertion step of a procedure for connecting proximal and middle phalanges of a foot with an implant in accordance with one or more embodiments of the present invention.

After the implant 14e is inserted into the middle phalanx 56, the handle 12e is removed and can be disposed. Subsequently, in one or more embodiments, the spacer 16e remains secured to the implant 14e, as schematically illustrated in FIG. 12. At this point in the procedure, the first portion of the implant 14e is exposed, while the second portion of the implant 14e is implanted in the middle phalanx 56. The exposed first portion of the implant 14e is subsequently implanted into the proximal phalanx 58. Additionally, the k-wire 70 also can protrude through the implant 14e.

Figure 13:
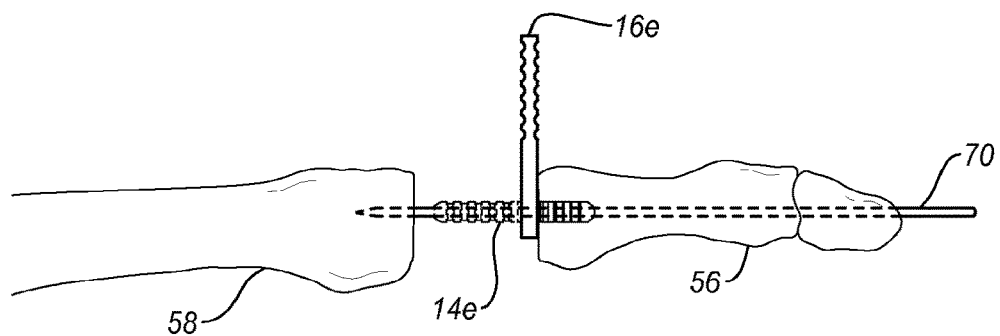
FIG. 13 illustrates a perspective view of a schematic representation of still another implant insertion step of a procedure for connecting proximal and middle phalanges of a foot with an implant in accordance with one or more embodiments of the present invention.
Figure 14:
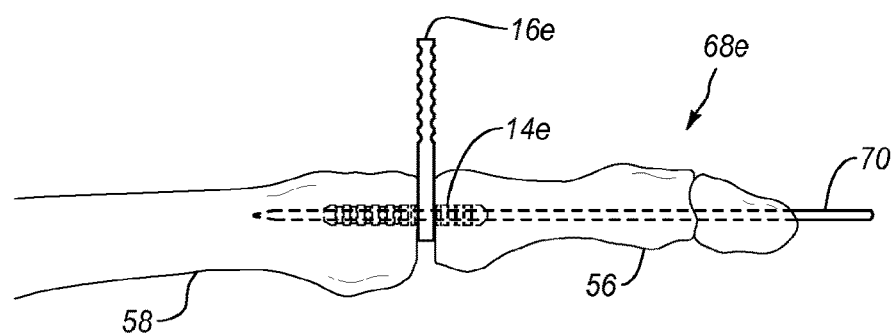
FIG. 14 illustrates a perspective view of a schematic representation of yet one other implant insertion step of a procedure for connecting proximal and middle phalanges of a foot with an implant in accordance with one or more embodiments of the present invention.

Subsequently, for example, as illustrated in FIG. 13, in at least one embodiment, the k-wire 70 is fitted into the proximal phalanx 58. Thereafter, the middle phalanx 56 together with the implant 14e and the spacer 16e are pushed toward the proximal phalanx 58, thereby driving and implanting the first portion of the implant 14e into the proximal phalanx 58, and forming a corrected toe 68e as schematically illustrated in FIG. 14. After the proximal phalanx 58 and the middle phalanx 56 are pushed together, the spacer 16e remains between the middle phalanx 56 and the proximal phalanx 58 for a time. As noted above, the spacer 16e ensures that the first and second portions of the implant 14e are implanted in the proximal phalanx 58 and in the middle phalanx 56, respectively.

Figure 15:
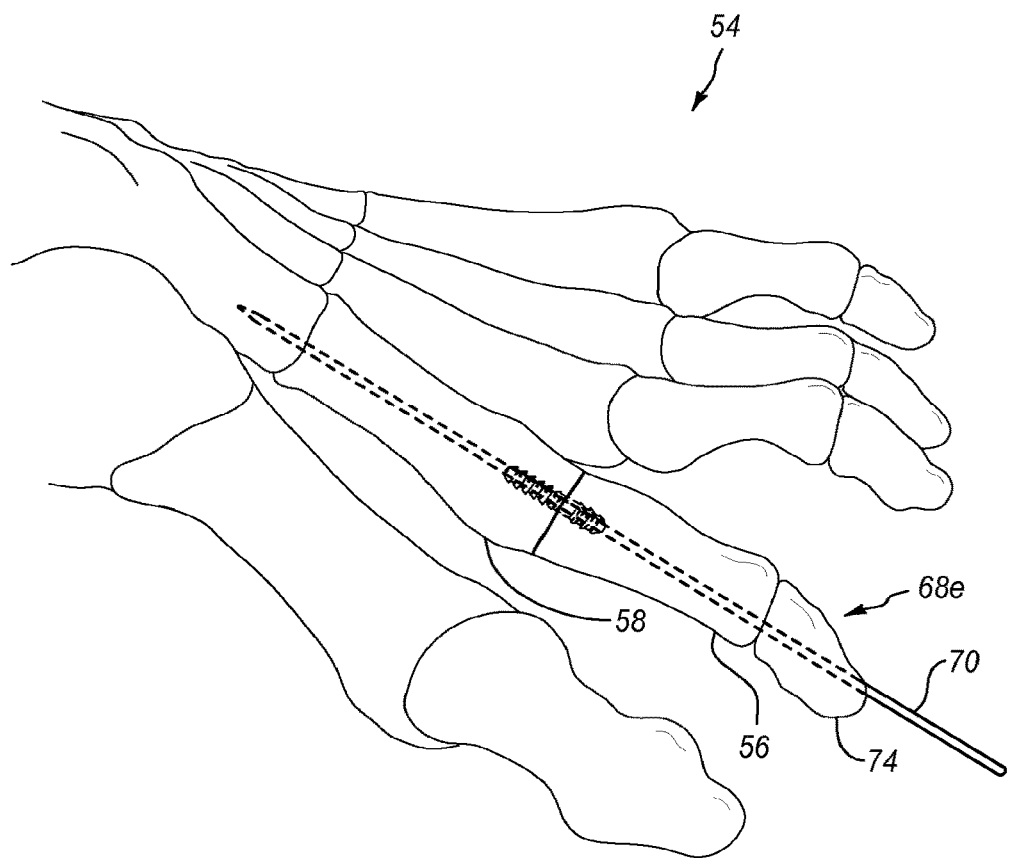
FIG. 15 illustrates a perspective view of a schematic representation of a foot after completion of a procedure for connecting proximal and middle phalanges of the foot in accordance with one or more embodiments of the present invention.

Subsequently, the spacer 16e is removed and the middle phalanx 56 and proximal phalanx 58 are further pushed together to close the gap previously occupied by the spacer 16e. As illustrated in FIG. 15, after the gap between the middle phalanx 56 and proximal phalanx 58 is closed, the corrected toe 68e faces substantially straight outward. As mentioned above, in some instances, the patient's foot 54 may have a more natural structure if the corrected toe 68e points slightly downward. Such downward orientation can be achieved by using a non-linear implant (described above). Alternatively, in some embodiments, such downward orientation of the corrected toe 68 is achieved by slightly bending the k-wire 70, thereby forcing at least the distal phalanx 74 downward.

In one or more embodiments, the k-wire 70 remains in the middle phalanx 56 and/or in the proximal phalanx 58 after completion of the procedure and is removed after the patient's foot 54 has healed. Alternatively, however, the k-wire 70 can be removed essentially immediately after the procedure is completed (i.e., after the middle phalanx 56 and the proximal phalanx 58 are pushed together to close the gap previously occupied by the spacer 16. Accordingly, the k-wire 70 can be used to guide the implant 14e into an appropriate position and/or to facilitate healing of the corrected toe 68 in a particular orientation (e.g., with the distal phalanx 74 facing more downward).

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

We claim:

1. An implant system for connecting two or more bone portions, the system comprising:
   an implant having a first portion, a second portion, and an intermediate portion between the first and second portions, the implant being configured to be implanted between a first and a second bone portions, wherein the first portion defines a slot; and
   a handle configured to be grasped by a user for inserting the second portion of the implant into the first bone portion, the handle having a rectangular hole therein that is configured to receive the first portion of the implant, wherein the hole includes a divider sized and configured to be received within the slot defined by the first portion of the implant, wherein the divider is configured to orient the implant,
   wherein the handle is configured to be removed from the first portion of the implant after inserting the second portion of the implant into the first bone portion.

2. The system as recited in claim 1 wherein the hole is configured to hold the implant in a predetermined orientation.

3. The system as recited in claim 2 wherein the handle has at least one orientation surface that corresponds with the orientation of the implant.

4. The system as recited in claim 1 wherein the implant is a cannulated implant having a passageway therethrough, and the passageway is configured to accept a k-wire.

5. The system as recited in claim 4 further comprising the k-wire, and the k-wire is configured to pass through the implant and to guide the implant.

6. The system as recited in claim 5 wherein the handle is configured to accommodate the k-wire.

7. The system as recited in claim 1 further comprising a spacer configured to be removably secured to the intermediate portion of the implant, wherein the spacer is configured to prevent insertion of the implant into the first bone portion beyond a length of the second portion of the implant.

8. The system as recited in claim 7 wherein the spacer is configured to prevent insertion of the implant into a second bone portion beyond a length of the first portion of the implant.

9. A system for correcting a hammer toe condition by fusing a middle phalanx to a proximal phalanx, the system comprising:
   an implant having a first barbed portion, a second barbed portion and an intermediate portion between the first and second barbed portions, wherein the first barbed portion defines a slot;
   a handle having a rectangular hole configured to receive the first barbed portion, wherein the hole includes a divider sized and configured to be received within the slot defined by the first portion of the implant, wherein the divider is configured to orient the implant, the handle configured to be grasped by a user;

a spacer configured to be removably coupled to the intermediate portion of the implant, wherein:
   the second barbed portion of the implant is configured to be secured within one of said middle phalanx or said proximal phalanx,
   the first barbed portion of the implant is configured to be removed from the handle and then inserted into the other of said middle phalanx or said proximal phalanx.

10. The system as recited in claim 9 wherein the implant is an angled implant, having an angle formed between the first barbed portion and the second barbed portion.

11. The system as recited in claim 9 wherein the implant is a cannulated implant having a passageway therethrough, and the passageway is configured to accept a k-wire.

12. The system as recited in claim 9 wherein the second barbed portion of the implant comprises a plurality of barbs forming a thread.

13. The system as recited in claim 12 wherein the hole of the handle is further configured to prevent the implant from rotating within the hole when the implant is secured within one of said middle phalanx or said proximal phalanx by screwing the implant into one of said middle phalanx or said proximal phalanx.

14. The system as recited in claim 9 wherein the handle has at least one orientation surface that corresponds with the orientation of the implant.

15. A method for implanting an implant between first and second bone portions, the method comprising:
   providing an implant having a first portion, a second portion, and an intermediate portion between the first and second portions, wherein the first portion defines a slot;
   providing a handle configured to be grasped by a user, the handle having a rectangular hole therein that is configured to receive one or more of the first portion, the second portion, and the intermediate portion of the implant, wherein the hole includes a divider sized and configured to be received within the slot defined by the first portion of the implant, and wherein the divider is configured to orient the implant;
   positioning at least a part of the first portion of the implant within the hole of the handle, such that a user can grasp the handle and manipulate the implant with the handle;
   inserting the second portion of the implant into the first bone portion;
   removing the handle from the first portion of the implant; and
   positioning the first portion of the implant within the second bone portion.

16. The method as recited in claim 15 wherein the implant has barbs on the first portion and on the second portion.

17. The method as recited in claim 15 wherein the hole is configured to hold the implant in a predetermined orientation and wherein the handle has at least one orientation surface that corresponds with the orientation of the implant.

18. The method as recited in claim 17 further comprising using the orientation surface of the hand to orient the second portion of the implant with respect to the first bone portion.

19. The method as recited in claim 15 wherein the implant is a cannulated implant having a passageway therethrough, and wherein the passage is configured to accept a k-wire.

20. The method as recited in claim 19 further comprising:
   inserting a k-wire into one or more of the first bone portion and the second bone portion; and
   guiding the implant over the inserted k-wire into the one or more of the first bone portion and the second bone portion.

* * * * *